United States Patent [19]

Muldrow, Jr.

[11] 4,279,806
[45] Jul. 21, 1981

[54] ANTIMONY MERCAPTIDES AS PROCESSING STABILIZERS FOR VINYL HALIDE RESINS

[75] Inventor: Charles N. Muldrow, Jr., East Windsor, N.J.

[73] Assignee: Associated Lead Inc., Philadelphia, Pa.

[21] Appl. No.: 63,597

[22] Filed: Aug. 8, 1979

Related U.S. Application Data

[63] Continuation-in-part of Ser. No. 936,121, Aug. 23, 1978, abandoned.

[51] Int. Cl.³ .......................... C08K 5/59; C07D 9/90
[52] U.S. Cl. .............................. 260/45.75 B; 260/446
[58] Field of Search .................. 260/45.75 B, 446; 424/296

[56] References Cited

U.S. PATENT DOCUMENTS

| | | | |
|---|---|---|---|
| 2,510,738 | 6/1950 | Clemence et al. | 260/45.75 B |
| 2,641,588 | 6/1953 | Leistner et al. | 260/45.75 B |
| 2,680,726 | 6/1954 | Weinberg et al. | 260/446 |
| 2,684,956 | 7/1954 | Weinberg et al. | 260/45.75 B |
| 3,525,760 | 8/1970 | Seki et al. | 260/45.75 S |
| 3,525,761 | 8/1970 | Seki et al. | 260/45.75 S |
| 4,029,618 | 6/1977 | Dieckmann | 260/45.75 B |

Primary Examiner—V. P. Hoke
Attorney, Agent, or Firm—Kenyon & Kenyon

[57] ABSTRACT

Novel compositions and use therefore as stabilizers during the production of vinyl halide resins are disclosed which comprise antimony mercaptides having the general formula:

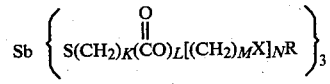

wherein
K is 1 to 4;
L is 0 to 1;
M is 1 to 4;
N is 1 to 4;
X is oxygen or sulfur; and
R is an alkyl, alkenyl, alkynyl having 1 to 18 carbon atoms and combinations thereof.

Such compositions when used during vinyl halide resin processing retard discoloration and mechanical degradation at least as effectively as previously known antimony mercaptides while being more economical to produce.

8 Claims, No Drawings

ANTIMONY MERCAPTIDES AS PROCESSING STABILIZERS FOR VINYL HALIDE RESINS

This application is a continuation-in-part application of application Ser. No. 936,121 filed on Aug. 23, 1978 abandoned.

The present invention relates to novel compositions and their use in the production of vinyl halide resins, and more particularly, polyvinyl chloride. The antimony mercaptides of the present invention are prepared from mercaptans that contain one or more aliphatic ether or thioether groups and may contain one or more carboxylic acid ester groups.

The use of antimony mercaptides as stabilizers for vinyl halide resins to guard against degradation by heat during molding and working of the resin into useful articles is known. For example, U.S. Pat. Nos. 2,680,726; 2,684,956; and 3,340,285; 3,399,220; 3,466,261; and 3,530,158 all disclose antimony organic sulphur-containing compounds as well as acknowledging their utility as stabilizers. Most recently, in U.S. Pat. Nos. 3,887,508 and 4,029,618, improved antimony mercaptides are disclosed which purportedly overcome various shortcomings, including high cost, said to exist in the other prior art materials, noteably, the propensity of such compounds to exude from molded or worked polyvinyl chloride plastic stock. The antimony mercaptides disclosed in the last two mentioned patents include, among others, antimony isooctyl thioglycolate.

A new class of antimony mercaptides has now been discovered which show color and heat stability results during vinyl halide resin processing which are at least equivalent to, and in some cases superior to, the results obtained with the prior art materials. More particularly, the antimony mercaptides of the present invention have the general formula:

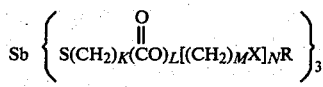

wherein
K is 1 to 4;
L is 0 to 1;
M is 0 to 4;
N is 1 to 4;
X is oxygen or sulfur; and
R is an alkyl, alkenyl, alkynyl having 1 to 18 carbon atoms and combinations thereof.

The selection of the particular antimony mercaptide species is critical to the extent necessary to enable the preparation of an effective stabilizer having an essentially colorless nature, and ability to maintain a liquid state under high relative humidity-temperature storage conditions without the production of solid degradation products.

The mercaptide groups $[S(CH_2)_K]$ of the invention are linked to the antimony primarily through covalent bonding. Such mercaptides must contain 1 to 4 carbon atoms as an alkylene group. Exemplary species include methylene, ethylene, 1,3-propylene, and 1,4-butylene. Alkylene groups having greater than 4 carbon atoms, while feasible, are not commercially available.

The carboxylic acid ester group $$[(CO)_L]$$

of the invention, if present, is linked to the mercaptide group through a carbon atom on the carboxylic acid ester moiety and linked through the acid ester to the remainder of the composition. The compositions of the invention may be prepared without the presence of such carboxylic acid ester group to yield effective materials.

The ether and thioether groups $[(CH_2)_M X]_N$ of the invention are linked to the carboxylic acid ester group and the alkyl, alkenyl, alkynyl groups discussed below. Such ether and thioether groups must contain 1 to 4 carbon atoms, one of the carbon atoms being linked to the carboxylic acid ester group. Exemplary species include methylene ether, methylene thioether, ethylene ether, ethylene thioether, 1,3-propylene ether, 1,3-propylene thioether, 1,4-butylene ether, and 1,4-butylene thioether. Alkylene ethers and thioethers having greater than 4 carbon atoms, while feasible, are not commercially available.

The ether and thioether groups may be repeative groups having 1 to 4 units of the aforementioned species.

The R group in the antimony mercaptides of this invention contain 1 to 18 carbon atoms and may comprise an alkyl, alkenyl and alkynyl moiety as well as combinations thereof. In the case where the R is an alkyl group, exemplary species include methyl, ethyl, n-propyl, n-butyl, n-pentyl, n-hexyl, n-octyl, n-nonyl, n-decyl, n-dodecyl, n-tetradecyl, n-hexadecyl and n-octadecyl. Preferred alkyl moieties are selected from those groups having 2 to 8 carbon atoms. In the case where the R is an alkenyl group, exemplary species include allyl, crotyl, 1-butenyl and 2-pentenyl. In the case where the R is an alkynyl group, exemplary species include 2-propynyl, 2-butynyl, and 2-pentynyl. Preferred alkenyl and alkynyl moities are selected from these groups having 2 to 8 carbon atoms.

Specific examples of the ether or thioether antimony mercaptides which are within the scope of this invention include, but are not limited to, the following: antimony 2-butoxyethyl thioglycolate, antimony 2-ethoxyethyl thioglycolate, antimony 2-methoxyethyl thioglycolate, antimony 2-hexoxyethyl thioglycolate, antimony butoxyethoxyethyl thioglycolate, antimony methoxyethoxyethyl thioglycolate, antimony ethoxyethoxyethyl thioglycolate, antimony ethylthioethyl thioglycolate, antimony methyltriethylene glycol thioglycolate, antimony ethyltriethylene glycol thioglycolate, and antimony dodecoxyethyl mercaptide.

The antimony mercaptides of the present invention may be prepared in any suitable manner. For example, when preparing the carboxylic acid ester compounds, the compositions are prepared by reacting thioglycolic acid or mercaptopropionic acid with an ether- or thioether-containing alcohol, preferably in the presence of a conventional acid catalyst. The reaction is performed under mild heating conditions, that is 20° C. to 110° C. with stirring. The resultant reaction product is then reacted with a source of trivalent antimony. More particularly, such subsequent reaction can be with a compound such as an antimony trialkoxide such as antimony tributoxide, an antimony carboxylate such as antimony triacetate, or a compound such as antimony oxide. On a commercial scale, the use of antimony oxide is preferred since it is less expensive and easier to obtain than compounds such as the antimony tributoxide. This reaction is performed with mild heat, that is 20° C. to 125° C. under agitation for 1 to 12 hours, to complete the reaction.

When preparing the ether or thioether compounds, a vinyl alkyl ether is preferably first reacted with hydrogen sulfide to form an alkoxyethyl mercaptan which product is then reacted with the trivalent antimony as discussed above. The reaction with hydrogen sulfide is preferably performed under pressure by conventional techniques until completion.

In another aspect of the present invention, stabilized vinyl halide resin compositions are provided which incorporate from about 0.01 to 3 PHR (parts per 100 parts resin) of the novel antimony mercaptides described hereinabove, and preferably from about 0.5 to 2 PHR. The procedures for preparing such vinyl halide compositions, and particularly polyvinyl chloride, are well-known in the art as described, for example, in U.S. Pat. Nos. 2,680,726; 2,604,458 and 4,029,618 hereby incorporated by reference. The novel compounds of this invention may be used alone or in combination with other compatible stabilizers, such as conventional organic stabilizers for vinyl halide resins, such as epoxides, organic phosphites and phenolics according to known procedures.

The compounds of the invention exhibit superior product color to the closest prior art material, namely off-white, for the inventive ether and thioether containing antimony mercaptides in comparison to a distinct yellow color for the prior art antimony isooctyl thioglycolate. This color property is an important factor affecting consumer choice of a vinyl halide resin stabilizer.

Another unexpected advantage derived from the inventive composition arises from their stability under high relative humidity-temperature storage conditions. This is surprising in view of the presence of ether or thioether groups which are known to absorb water. This phenomena was demonstrated in two different series of experiments to test storage stability at 30° C. and 100% relative humidity. Comparative antimony (III) isooctyl thioglycolate started separating solid degradation products within 8 days, whereas a similarly treated inventive antimony (III) butoxyethyl thioglycolate maintained its liquid state for the entire experiment, i.e. for 30 days. The solid degradation products of the reference material were partly hydrolyzed and more soluble in water.

The following examples are given to illustrate the invention and particularly the methods of synthesizing the novel antimony mercaptides of the present invention, it being understood that such examples are illustrative only and are not deemed to be limiting thereof. All percentages given are based upon weight unless otherwise indicated.

EXAMPLE I

Thioglycolic acid obtained from Evans Chemetics, Inc. (71.96 g, 0.781 mole) was added to 2-butoxyethanol (scintilation grade) obtained from Eastman Kodak Company (92.33 g, 0.781 mole) utilizing 10% Dowex HGR-W-H cation exchange resin (calculated on the alcohol) as a catalyst. The mixture was vigorously stirred while maintaining a nitrogen atmosphere. After total addition of reactants, a temperature rise of 4° C. occurred. Thereafter, the solution was heated and the byproduct of the reaction, water, was distilled over at 98° C. and collected in a graduated receiver. After three hours, 96.5% of the water distillate was collected. Unreacted starting materials were separated from the product by vacuum distillation and a weight of 105.8 g of product, i.e. 2-butoxyethanol thioglycolate, was collected.

Antimony tributoxide obtained from Alfa Products, Ventron Corporation (39.72 g, 0.117 mole) was added dropwise to the 2-butoxyethanol thioglycolate (67.37 g, 0.350 mole) and the mixture vigorously stirred while maintaining a nitrogen atmosphere. Upon addition of the reactants there was an immediate 25° C. temperature rise. The solution was further heated, and the byproduct of the reaction, 1-butanol, was distilled over at 47° C. at 7 mm of Hg pressure and collected in a graduated receiver. After 4.5 hours, 78.78 g (96.0% yield) of the product, antimony 2-butoxyethyl thioglycolate, had formed.

EXAMPLE II

Thioglycolic acid (1687.2 g, 14.28 mole) obtained from Evans Chemetics, Inc. was further purified by vacuum distillation and added to 2-butoxyethanol (butyl Cellosolve) obtained from Union Carbide Corporation (1315.0 g, 14.28 mole) with 12% Dowex 50W X12 cation exchange resin (calculated on the alcohol) as a catalyst. Cellosolve is a trademark of Union Carbide Corporation for monoalkyl ethers of glycol. Dowex is a trademark of Dow Chemical Corporation for a sulfonated polystyrene resin. The mixture was vigorously stirred and a nitrogen atmosphere maintained. After total addition of the reactants, a temperature rise of 5° C. was observed. The solution was heated and the byproduct of the reaction, water, was distilled over with 2-butoxyethanol at 102° C. and collected in a graduated receiver. After 15 hours the catalyst was removed. Subsequently, unreacted starting materials were separated from the product by vacuum distillation and a weight of 2011.9 g of the product, 2-butoxyethyl-thioglycolate, was collected.

NL Industries, Inc. antimony oxide (508.3 g, 1.744 mole) was added to the 2-butoxyethyl thioglycolate (2011.8 g, 10.462 mole) and the mixture moderately stirred while a nitrogen atmosphere was maintained. Upon addition of the reactants there was an immediate 35° C. temperature rise. The mixture was further heated and the byproduct, water, was distilled over at 47°C. at 75 mm of Hg pressure into a graduated receiver. After 6 hours, 2412.5 g. (99.4% yield) of the product, antimony 2-butoxyethyl thioglycolate had formed.

EXAMPLE III

Thioglycolic acid obtained from Evans Chemetics, Inc. (33.13 g, 0.360 mole) was added to butoxyethoxyethanol (butyl Carbitol) (58.32 g, 0.360 mole) obtained from Sargent-Welch Scientific Company with 3% toluenesulfonic acid (1.74 g) as a catalyst. Carbitol is a trademark of Union Carbide Corporation for monoalkyl ethers of diethyleneglycol. The mixture was vigorously stirred while maintaining a nitrogen atmosphere. Upon addition of the reactants, there was an immediate 8° C. increase in temperature. The solution was further heated and the byproduct of the reaction, water, was distilled over at 93° C. and collected in a graduated receiver. After 3 hours, 84.87 g (97.5% yield) of the product, butoxyethoxyethyl thioglycolate, had formed.

Antimony tributoxide (12.5 ml, 0.339 mole) obtained from Stauffer Chemical Company was added directly to the butoxyethyoxyethyl thioglycolate (30 g, 1.017 mole) previously obtained and an immediate 20° C. temperature increase was observed. The mixture was vigorously stirred and a nitrogen atmosphere maintained. The solution was then further heated and a vacuum of 20-40 mm was applied to the system. The byproduct of the reaction, n-butanol, was distilled over at 20° C. and collected. After 3 hours, the yield of antimony butoxyethoxyethyl thioglycolate was 91.3%.

EXAMPLE IV

Thioglycolic acid (40.9 ml, 0.589 mole) obtained from Evans Chemetics, Inc. was added dropwise with stirring to butoxyethoxyethanol (butyl Carbitol) (95.53 g, 0.589 mole) obtained from Fisher Scientific Company with 12% Dowex cation exchange resin HGR-W (10% crosslinking, 11.46 g) as a catalyst. A temperature increase of 6° C. occurred immediately upon addition of the reactants. The solution was further heated and the byproduct, water, was distilled over at 89° C. and collected. When 50% of the water had been collected, a 30% excess of butoxyethoxyethanol (33 mls) was added to increase the rate of product formation. After 3.5 hours a 92.4% yield of butoxyethoxyethyl thioglycolate was obtained and thereafter vacuum distilled at 10 mm Hg and a temperature range of 25°-100° C. in order to remove the unreacted starting materials.

Antimony oxide obtained from NL Industries, Inc. (21.95 g, 0.0752 mole) was placed in the reaction vessel and one-half (50 ml) of the butoxyethoxyethyl thioglycolate added and stirred. A temperature rise of 13° C. was observed. The remaining 50 ml of the butoxyethoxyethyl thioglycolate was added dropwise over 0.5 hours and the reaction mixture vigorously stirred while maintaining a nitrogen atmosphere. The solution was heated and an absolute pressure of 60 mm Hg was applied to the system. The byproduct, water, was distilled over at 35° C. and collected. After one hour, the yield of antimony butoxyethoxyethyl thioglycolate was 92%. The resultant product was filtered to remove the unreacted antimony oxide.

In order to demonstrate the effectiveness of the novel compounds of the present invention as stabilizers in the production of vinyl halide resins, and particularly polyvinyl chloride, BRABENDER heat stability data was taken on various of the antimony mercaptides of the present invention in order to compare same with similar data taken for a commercial grade of antimony isooctyl thioglycolate and, in certain instances, experimentally produced antimony isooctyl thioglycolate. For each example, BRABENDER Plasti-Corder constants were 197° C., 48 cc 50 rpm, No. 6 oil head. For each of the following comparative examples, Table I gives results with a basic formulation including:
GEON 103 EPF 76: 100 PHR
OMYALITE 90-T: 2.5
TITANOX 2071: 1.0
Calcium Stearate: 0.7
165° Paraffin Wax: 1.0
PLASTIFLOW POP: 0.15
Sb Stabilizer: as shown GEON is a trademark of B. F. Goodrich Company for polyvinyl chloride resin.

OMYALITE is a trademark of PLUESS-STAUFFER for calcium carbonate having an average particle diameter of 0.7 microns.

TITANOX is a trademark of NL Industries for $TiO_2$.

PLASTIFLOW POP is a trademark of NL Industries for modified polyethylene wax.

Each Table II gives the results with the basic formulation including:
GEON 103 EPF 76: 100 PHR
OMYALITE 90-T: 2.5
TITANOX 2071: 1.0
PLASTIFLOW CW-2: 0.35
PLASTIFLOW POP: 0.5
Sb Stabilizer: as shown PLASTIFLOW CW-2 is a trademark of NL Industries, Inc. for an ester-wax.

The BRABENDER test method is performed as follows:

(1) Prepare a blend of all ingredients in a conventional PVC pipe formulation, such as herein described in the absence of the stabilizer.

(2) Add the antimony mercaptide stabilizer to aliquots of the blend at equal antimony values to yield 0.06 parts antimony per 100 parts resin.

(3) Place 48 cc of the stabilized resin in a No. 6 oil-heated BRABENDER Plasti-Corder equipped with a stirrer.

(4) The Plasti-Corder is operated at a rotor speed of 50 rpm and at a temperature of 197° C.

(5) During operation, fusion time, fusion torque, equilibrium torque and heat stabilities are measured and the test is terminated upon evolution of hydrogen chloride.

As can readily be seen by reference to the comparative examples, the results obtained during the experiments for both color break and heat stability indicate that the antimony mercaptides of the present invention exhibit properties which are at least equivalent to, and in some cases superior to, those obtained with the comparative antimony compounds. Further, the products of the present invention exhibit a hydrolytic stability as great as 2½ times that of the comparative material which is extremely important when considering practical commercial usages of the product with regard to handling and the like.

EXAMPLE V

This example demonstrates the preparation of an ether containing antimony mercaptan of this invention.

Blue Star antimony trioxide (8.52, 0.0292 mole) obtained from Anzon was placed in the reaction vessel and 2-mercaptoethyl n-dodecyl ether (50 ml, 0.1752 mole) from Phillips Petroleum Company added dropwise. The mixture was vigorously stirred while maintaining a nitrogen atmosphere and heated up to 120° C. for a total of 5½ hours. The byproduct of the reaction, water, was distilled over at 35° C. and collected. After one hour, the yield of Sb (III) mercaptoethyl dodecyl ether $[Sb(SCH_2CH_2O-n-C_{12}H_{25})_3]$ was 92.4%. The resultant product was filtered to remove the unreacted antimony oxide.

The invention being thus described, it will be obvious that the same may be varied in many ways. Such variations are not to be regarded as a departure from the spirit and scope of the invention, and all such modifications are intended to be included within the scope of the following claims.

COMPARATIVE EXAMPLE A

| TABLE I |
|---|
| BRABENDER |

-continued

| Antimony Mercaptides Type | Level PHR* | Plasti-Corder Color Break Min | Heat Stability Min |
|---|---|---|---|
| Commercial antimony isooctyl thioglycolate[1] | 0.50 | 8 | 10 |
| Antimony isooctyl thioglycolate | 0.37 | 8 | 10 |
| Antimony ethoxyethoxyethyl thioglycolate | 0.39 | 8 | 10 |
| Antimony butoxyethoxyethyl thioglycolate | 0.387 | 7 | 9 |
| Antimony 2-hexoxyethyl thioglycolate | 0.42 | 7 | 10 |

TABLE II

| | | | |
|---|---|---|---|
| Commercial antimony isooctyl thioglycolate[1] | 0.50 | 5 | 7 |
| Antimony isooctyl thioglycolate | 0.37 | 5 | 7 |
| Antimony ethoxyethoxyethyl thioglycolate | 0.39 | 5 | 7 |
| Antimony butoxyethoxyethyl thioglycolate | 0.387 | 5 | 6 |
| Antimony 2-hexoxyethyl thioglycolate | 0.42 | 5 | 7 |

[1]Average Value:
11.1% Antimony concentration
70.0% Antimony isooctyl thioglycolate
1% p-tert-butyl catacol
29% mineral oil
*The level PHR means that level of addition of equivalent antimony mercaptide to yield 0.06 PHR antimony.

COMPARATIVE EXAMPLE B

TABLE I

| Antimony Mercaptide Type | Form | Level PHR* | BRABENDER Plasti-Corder Color Break Min | Heat Stability Min |
|---|---|---|---|---|
| Commercial antimony isooctyl thioglycolate[1] | liquid | 0.5 | 8 | 11.2 |
| Antimony 2-butoxyethyl thioglycolate | liquid | 0.34 | 6 | 9.7 |

TABLE II

| Commercial antimony isooctyl thioglycolate[1] | liquid | 0.5 | 6 | 7.3 |
| Antimony 2-butoxyethyl thioglycolate | liquid | 0.34 | 5 | 7.0 |

[1]Average Value:
11.1% Antimony concentration
70.0% Antimony isooctyl thioglycolate
1% p-tert-butyl catacol
29% mineral oil
*The level PHR means that level of addition of equivalent antimony mercaptide to yield 0.06 PHR antimony.

COMPARATIVE EXAMPLE C

TABLE I

| Antimony Mercaptides Type | Level PHR* | BRABENDER Plasti-Corder Color Break Min | Heat Stability Min |
|---|---|---|---|
| Commercial antimony isooctyl thioglycolate[1] | 0.50 | 8 | 10.0 |
| Antimony 2-ethoxyethyl thioglycolate | 0.29 | 7 | 8.8 |
| Antimony 2-butoxyethyl thioglycolate | 0.35 | 7 | 8.7 |
| Antimony methoxyethoxyethyl thioglycolate | 0.37 | 7 | 8.7 |
| Antimony butoxyethoxyethyl thioglycolate | 0.44 | 7 | 8.5 |
| Antimony tetrahydrofurfuryl thioglycolate | 0.30 | 7 | 9.3 |

TABLE II

| Commercial antimony isooctyl thioglycolate[1] | 0.50 | 6 | 6.6 |
| Antimony 2-ethoxyethyl thioglycolate | 0.29 | 5 | 5.8 |
| Antimony 2-butoxyethyl thioglycolate | 0.35 | 5 | 6.3 |
| Antimony methoxyethoxyethyl thioglycolate | 0.37 | 5 | 6.0 |
| Antimony butoxyethoxyethyl thioglycolate | 0.44 | 5 | 5.9 |
| Antimony tetrahydrofurfuryl thioglycolate | 0.30 | 5 | 5.9 |

[1]Average Value:
11.1% Antimony concentration
70.0% Antimony isooctyl thioglycolate
1% p-tert-butyl catacol
29% mineral oil
*The level PHR means that level of addition of equivalent antimony mercaptide to yield 0.06 PHR antimony.

COMPARATIVE EXAMPLE D

TABLE I

| Antimony Mercaptides Type | Level PHR* | BRABENDER Plasti-Corder Color Break Min | Heat Stability Min |
|---|---|---|---|
| Commercial antimony isooctyl thioglycolate[1] | 0.50 | 8 | 10 |
| Antimony 2-butoxyethyl thioglycolate | 0.35 | 7 | 8 |
| Antimony 2-butoxyethyl thioglycolate** | 0.53 | 8 | 10 |
| Antimony 2-methoxyethyl thioglycolate | 0.28 | 6 | 8 |
| Antimony ethylthioethyl thioglycolate | 0.35 | 4 | 6 |

TABLE II

| Commercial antimony isooctyl thioglycolate[1] | 0.50 | 5 | 7 |
| Antimony 2-butoxyethyl thioglycolate | 0.35 | 5 | 6 |
| Antimony 2-butoxyethyl thioglycolate** | 0.53 | 7 | 8 |
| Antimony 2-methoxyethyl thioglycolate | 0.28 | 5 | 6 |
| Antimony ethylthioethyl thioglycolate | 0.35 | 3 | 5 |

**Contains 33.2% mineral oil and 0.7% 4-tertiary butylcatechol
[1]Average Value:
11.1% Antimony concentration
70.0% Antimony isooctyl thioglycolate
1% p-tert-butyl catacol
29% mineral oil
*The level PHR means that level of addition of equivalent antimony mercaptide to yield 0.06 PHR antimony.

What is claimed is:
1. A vinyl halide resin composition comprising a vinyl halide resin and a stabilizer composition which comprises an antimony mercaptide having the following formula:

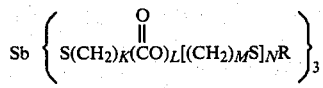

wherein
- K is 1 to 4;
- L is 0 to 1;
- M is 1 to 4;
- N is 1 to 4;
- R is an alkyl, alkenyl or alkynyl having 1 to 18 carbon atoms and combinations thereof.

2. A vinyl halide resin composition according to claim 1 in which the stabilizer composition comprises antimony ethylthioethyl thioglycolate.

3. A vinyl halide resin composition comprising a vinyl halide resin and a stabilizer which comprises an antimony mercaptide of the following formula:

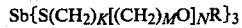

wherein
- K is 1 to 4;
- M is 1 to 4;
- N is 1 to 4;
- R is an alkyl, alkenyl or alknyl having 1 to 18 carbon atoms and combinations thereof.

4. A vinyl halide resin composition according to claim 3 in which the stabilizer composition comprises antimony dodecoxyethyl mercaptide.

5. A composition comprising an antimony mercaptide having the following formula:

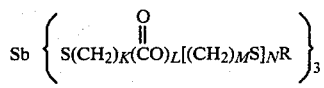

wherein
- K is 1 to 4;
- L is 0 to 1;
- M is 1 to 4;
- N is 1 to 4;
- R is alkyl, alkenyl, alkynyl having 1 to 18 carbon atoms and combinations thereof.

6. The composition of claim 5 which comprises antimony ethylthioethyl thioglycolate.

7. A composition comprising an antimony mercaptide having the following formula:

wherein
- K is 1 to 4;
- M is 1 to 4;
- N is 1 to 4;
- R is alkyl, alkenyl, alkynyl having 1 to 18 carbon atoms and combinations thereof.

8. The composition of claim 7 which comprises antimony dodecoxyethyl mercaptide.

* * * * *

UNITED STATES PATENT AND TRADEMARK OFFICE
CERTIFICATE OF CORRECTION

PATENT NO. : 4,279,806

DATED : July 21, 1981

INVENTOR(S) : Charles Norment Muldrow, Jr.

It is certified that error appears in the above—identified patent and that said Letters Patent is hereby corrected as shown below:

Column 1, line 6:

Change "a" to --A-- in the word "application".

Column 1, line 7:

After "Aug. 23, 1978" end sentence and omit the word "abandoned".

Column 3, line 40:

After "This" change "phenomena" to --phenomenon--.

Column 5, line 6:

After "20-40mm" insert --Hg--.

Column 6, line 11:

Change "trademarkof" to --trademark of--.

UNITED STATES PATENT AND TRADEMARK OFFICE
CERTIFICATE OF CORRECTION

PATENT NO. : 4,279,806

DATED : July 21, 1981

INVENTOR(S) : Charles Norment Muldrow, Jr.

It is certified that error appears in the above—identified patent and that said Letters Patent is hereby corrected as shown below:

Column 9, line 27:

After "alkenyl or" change "alknyl" to --alkynyl--.

Signed and Sealed this

First Day of December 1981

[SEAL]

*Attest:*

*Attesting Officer*

GERALD J. MOSSINGHOFF

*Commissioner of Patents and Trademarks*